(12) United States Patent
Johnson et al.

(10) Patent No.: US 10,278,675 B2
(45) Date of Patent: May 7, 2019

(54) IMPLANTABLE ESTRUS DETECTION DEVICES, SYSTEMS, AND METHODS

(71) Applicant: PALO ALTO RESEARCH CENTER INCORPORATED, Palo Alto, CA (US)

(72) Inventors: David Mathew Johnson, San Francisco, CA (US); Scott A. Uhland, San Jose, CA (US); Ramkumar Abhishek, Mountain View, CA (US); Robert Thomas Krivacic, San Jose, CA (US); Martin Sheridan, Redwood City, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 1094 days.

(21) Appl. No.: 14/448,074

(22) Filed: Jul. 31, 2014

(65) Prior Publication Data

US 2016/0030010 A1    Feb. 4, 2016

(51) Int. Cl.
*A61B 10/00* (2006.01)
*A61D 19/02* (2006.01)
(Continued)

(52) U.S. Cl.
CPC ...... *A61B 10/0012* (2013.01); *A61B 5/02055* (2013.01); *A61B 5/076* (2013.01);
(Continued)

(58) Field of Classification Search
CPC . A61B 5/6843; A61B 5/7275; A61B 2562/08; A61B 2562/164; A61B 5/4839
(Continued)

(56) References Cited

U.S. PATENT DOCUMENTS 3,811,443 A * 5/1974 Dickinson, III ......... A61D 7/00
600/35
3,844,273 A * 10/1974 Polson ................. A61B 5/0008
119/51.02
(Continued)

FOREIGN PATENT DOCUMENTS

DE       4130843 A1    3/1993
WO    94/01165 A1    1/1994
(Continued)

OTHER PUBLICATIONS

U.S. Appl. No. 14/071,929, Abhishek et al.
(Continued)

*Primary Examiner* — May A Abouelela
(74) *Attorney, Agent, or Firm* — Hollingsworth Davis, LLC (57) ABSTRACT

Devices, systems, and methods for detecting estrus in subjects are provided. Devices include a housing configured for intravaginal/intrauterine deployment and retention and a sensor disposed in or on the housing, and are configured to use condition information sensed by the sensor to determine an estrus condition of the subject. Methods include deploying a device in the subject, sensing the condition information, and determining an estrus condition using the condition information. Systems include a device configured to communicate with a base station and/or with other implanted devices, which are located within a reception radius thereof, regarding the determined estrus condition.

18 Claims, 6 Drawing Sheets

(51) Int. Cl.
  *A61D 19/04* (2006.01)
  *A61B 5/0205* (2006.01)
  *A61B 5/07* (2006.01)
  *A61D 17/00* (2006.01)
  *A61B 5/1459* (2006.01)
  *A61B 5/1455* (2006.01)
  *A61B 5/11* (2006.01)
  *A61B 5/03* (2006.01)
  *A61B 5/00* (2006.01)
  *A61B 5/024* (2006.01)
  *A61B 5/103* (2006.01)

(52) U.S. Cl.
  CPC ......... *A61D 17/002* (2013.01); *A61D 19/027* (2013.01); *A61D 19/04* (2013.01); *A61B 5/02416* (2013.01); *A61B 5/035* (2013.01); *A61B 5/1032* (2013.01); *A61B 5/1118* (2013.01); *A61B 5/1459* (2013.01); *A61B 5/14551* (2013.01); *A61B 5/14552* (2013.01); *A61B 5/4839* (2013.01); *A61B 2010/0016* (2013.01); *A61B 2010/0019* (2013.01); *A61B 2503/40* (2013.01)

(58) Field of Classification Search
  USPC .................... 600/300, 301, 551; 607/28
  See application file for complete search history.

(56) References Cited

U.S. PATENT DOCUMENTS

| | | | |
|---|---|---|---|
| 4,206,766 A * | 6/1980 | Bielka | A61D 17/002 600/551 |
| 4,304,232 A | 12/1981 | Michaels | |
| 4,308,867 A | 1/1982 | Roseman et al. | |
| 4,402,695 A | 9/1983 | Wong | |
| 4,455,610 A * | 6/1984 | Rodrian | A01K 11/006 377/6 |
| 4,503,808 A * | 3/1985 | McAlister | A61D 17/002 600/551 |
| 4,635,587 A * | 1/1987 | Leonardo | A61D 17/002 340/573.3 |
| 4,685,421 A * | 8/1987 | Colburn, Jr. | A01K 11/005 600/551 |
| 4,687,423 A | 8/1987 | Maget et al. | |
| 4,696,258 A * | 9/1987 | Magrath | A01K 11/005 600/551 |
| 4,846,106 A * | 7/1989 | Leonardo | A61D 19/00 600/551 |
| 4,886,514 A | 12/1989 | Maget | |
| 4,892,778 A | 1/1990 | Theeuwes et al. | |
| 4,895,165 A * | 1/1990 | Blair | A61B 10/0012 600/551 |
| 4,902,278 A | 2/1990 | Maget et al. | |
| 5,002,540 A | 3/1991 | Brodman et al. | |
| 5,062,834 A | 11/1991 | Gross et al. | |
| 5,090,963 A | 2/1992 | Gross et al. | |
| 5,111,799 A * | 5/1992 | Senger | A61D 17/002 600/551 |
| 5,112,614 A | 6/1992 | Magruder et al. | |
| 5,135,499 A | 8/1992 | Tafani et al. | |
| 5,162,116 A | 9/1992 | Shepherd et al. | |
| 5,216,599 A * | 6/1993 | Uebe | A61B 10/0012 128/920 |
| 5,318,557 A | 6/1994 | Gross | |
| 5,354,264 A | 10/1994 | Bae et al. | |
| 5,415,629 A | 5/1995 | Henley | |
| 5,522,804 A | 6/1996 | Lynn | |
| 5,542,431 A * | 8/1996 | Starzl | A61B 10/0012 119/174 |
| 5,566,679 A * | 10/1996 | Herriott | A61D 17/002 600/551 |
| 5,593,552 A | 1/1997 | Joshi et al. | |
| 5,780,058 A | 7/1998 | Wong et al. | |
| 5,816,248 A | 10/1998 | Anderson et al. | |
| 5,881,673 A * | 3/1999 | Beach | A61D 17/002 119/174 |
| 5,928,195 A | 7/1999 | Malamud et al. | |
| 5,951,538 A | 9/1999 | Joshi et al. | |
| 6,030,375 A | 2/2000 | Anderson et al. | |
| 6,086,909 A | 7/2000 | Harrison et al. | |
| 6,139,538 A | 10/2000 | Houghton et al. | |
| 6,183,434 B1 | 2/2001 | Eppstein | |
| 6,322,532 B1 | 11/2001 | D'Sa et al. | |
| 6,352,524 B1 | 3/2002 | Bunt | |
| 6,423,039 B1 | 7/2002 | Rathbone et al. | |
| 6,444,224 B1 | 9/2002 | Rathbone et al. | |
| 6,450,991 B1 | 9/2002 | Bunt et al. | |
| 6,532,386 B2 | 3/2003 | Sun et al. | |
| 6,591,133 B1 | 7/2003 | Joshi | |
| 6,638,246 B1 | 10/2003 | Naimark et al. | |
| 6,743,211 B1 | 6/2004 | Prausnitz et al. | |
| 6,756,053 B2 | 6/2004 | Zhang et al. | |
| 6,776,164 B2 | 8/2004 | Bunt et al. | |
| 6,805,877 B2 | 10/2004 | Massara et al. | |
| 6,835,392 B2 | 12/2004 | Hsu et al. | |
| 6,925,417 B2 * | 8/2005 | Sasaguri | A61D 17/008 119/174 |
| 6,962,579 B2 | 11/2005 | Jellie | |
| 6,978,172 B2 | 12/2005 | Mori et al. | |
| 7,004,171 B2 | 2/2006 | Benita et al. | |
| 7,083,575 B1 | 8/2006 | Claycomb et al. | |
| 7,083,590 B1 | 8/2006 | Bunt et al. | |
| 7,137,359 B1 * | 11/2006 | Braden | A61D 17/002 119/854 |
| 7,427,271 B2 * | 9/2008 | Kirsner | A61B 10/0012 600/300 |
| 7,486,989 B2 | 2/2009 | Sun et al. | |
| 7,497,855 B2 | 3/2009 | Ausiello et al. | |
| 7,732,408 B2 | 6/2010 | Josephson et al. | |
| 8,070,687 B2 * | 12/2011 | Cinti | A61B 10/0012 600/504 |
| 8,346,483 B2 * | 1/2013 | Kil | G01N 1/06 702/19 |
| 8,551,012 B2 * | 10/2013 | Signorini | A61B 17/43 119/174 |
| 9,119,379 B1 * | 9/2015 | Yancey | A61B 5/0004 |
| 9,297,083 B2 * | 3/2016 | Abhishek | C25B 9/063 |
| 9,603,691 B2 * | 3/2017 | Rajkondawar | A61D 17/002 |
| 2002/0010390 A1 * | 1/2002 | Guice | A01K 11/008 600/300 |
| 2002/0010414 A1 | 1/2002 | Coston et al. | |
| 2002/0045883 A1 | 4/2002 | Jellie et al. | |
| 2002/0156394 A1 * | 10/2002 | Mehrotra | A61D 17/002 600/551 |
| 2003/0018295 A1 | 1/2003 | Henley et al. | |
| 2003/0130558 A1 | 7/2003 | Massara et al. | |
| 2003/0219472 A1 | 11/2003 | Paulelli et al. | |
| 2004/0059388 A1 | 3/2004 | Herbst et al. | |
| 2004/0082937 A1 | 4/2004 | Ausiello et al. | |
| 2004/0087893 A1 | 5/2004 | Kwon | |
| 2004/0219192 A1 | 11/2004 | Horstmann et al. | |
| 2005/0000514 A1 | 1/2005 | Sullivan et al. | |
| 2005/0027208 A1 * | 2/2005 | Shiraishi | E03D 9/08 600/551 |
| 2005/0054969 A1 | 3/2005 | Hoff et al. | |
| 2005/0124875 A1 | 6/2005 | Kawano et al. | |
| 2005/0165326 A1 * | 7/2005 | Kirsner | A61B 10/0012 600/551 |
| 2005/0244502 A1 | 11/2005 | Mathias et al. | |
| 2005/0256423 A1 * | 11/2005 | Kirsner | A61B 5/053 600/551 |
| 2005/0267440 A1 | 12/2005 | Herman et al. | |
| 2006/0024358 A1 | 2/2006 | Santini et al. | |
| 2006/0184092 A1 | 8/2006 | Atanasoska et al. | |
| 2007/0038181 A1 | 2/2007 | Melamud et al. | |
| 2007/0173711 A1 | 7/2007 | Shah et al. | |
| 2007/0225634 A1 | 9/2007 | Ferren et al. | |
| 2007/0269385 A1 | 11/2007 | Yun et al. | |
| 2008/0004564 A1 | 1/2008 | Smith | |
| 2008/0004596 A1 | 1/2008 | Yun et al. | |

(56) References Cited

U.S. PATENT DOCUMENTS

| | | | |
|---|---|---|---|
| 2008/0071190 A1* | 3/2008 | Gorodeski | A61B 5/14539 600/551 |
| 2008/0171950 A1 | 7/2008 | Franco | |
| 2008/0228058 A1* | 9/2008 | Cinti | A61D 17/002 600/368 |
| 2008/0262412 A1 | 10/2008 | Atanasoska et al. | |
| 2008/0269666 A1 | 10/2008 | Wang et al. | |
| 2009/0043174 A1* | 2/2009 | Jarrell | A61B 5/05 600/300 |
| 2009/0048498 A1* | 2/2009 | Riskey | A61B 5/0031 600/302 |
| 2009/0131737 A1 | 5/2009 | Ferren et al. | |
| 2009/0171315 A1 | 7/2009 | Versi | |
| 2009/0187392 A1* | 7/2009 | Riskey | A01K 11/007 703/11 |
| 2009/0281528 A1 | 11/2009 | Grovender | |
| 2009/0306633 A1 | 12/2009 | Trovato et al. | |
| 2009/0308752 A1 | 12/2009 | Evans | |
| 2010/0036212 A1* | 2/2010 | Rieth | A61B 5/01 600/301 |
| 2010/0036279 A1* | 2/2010 | Rieth | A61B 5/01 600/551 |
| 2011/0087155 A1 | 4/2011 | Uhland et al. | |
| 2011/0087192 A1 | 4/2011 | Uhland et al. | |
| 2011/0087195 A1 | 4/2011 | Uhland et al. | |
| 2011/0092906 A1 | 4/2011 | Boettger | |
| 2012/0157856 A1* | 6/2012 | An | A61B 5/024 600/484 |
| 2012/0238912 A1 | 9/2012 | Rajkondawar et al. | |
| 2013/0079599 A1* | 3/2013 | Holmes | G06F 19/3418 600/300 |
| 2013/0137940 A1* | 5/2013 | Schafer | A61B 10/0012 600/301 |
| 2013/0211372 A1 | 8/2013 | Rosenshein | |
| 2013/0338531 A1* | 12/2013 | Regas | A61D 17/002 600/551 |
| 2014/0088345 A1 | 3/2014 | Uhland et al. | |
| 2014/0088346 A1 | 3/2014 | Uhland et al. | |
| 2014/0088486 A1 | 3/2014 | Uhland et al. | |
| 2014/0200553 A1 | 7/2014 | Johnson et al. | |
| 2014/0273824 A1* | 9/2014 | Fenner | H04B 5/0031 455/41.1 |
| 2014/0338447 A1* | 11/2014 | Sharpe | A01K 29/005 73/431 |
| 2015/0088216 A1* | 3/2015 | Gordon | A61N 1/3704 607/14 |
| 2015/0224302 A1* | 8/2015 | Gunderson | A61N 1/08 607/28 |

FOREIGN PATENT DOCUMENTS

| | | | |
|---|---|---|---|
| WO | 94/18952 A1 | 9/1994 | |
| WO | 97/41831 A1 | 11/1997 | |
| WO | 01/12101 A1 | 2/2001 | |
| WO | 2005/056708 A2 | 6/2005 | |
| WO | 2005/089728 A2 | 9/2005 | |
| WO | 2007/041119 A1 | 4/2007 | |
| WO | 2007/047811 A2 | 4/2007 | |
| WO | 2007/140416 A2 | 12/2007 | |
| WO | 2009/081411 A2 | 7/2009 | |
| WO | 2010/048478 A2 | 4/2010 | |

OTHER PUBLICATIONS

U.S. Appl. No. 14/107,367, Abhishek et al.

Boehmer et al., "Effects of Temperature of Consumed Water on Rumen Temperature of Beef Cows," Oklahoma Agricultural Experiment Station, 2009, 4 pages.

Boehmer, "Ruminal Temperature for Identification and Prediction of Estrus in Beef Cows," 2012, Thesis.

Heckman et al., "Estrous Cycle Patterns in Cattle Monitored by Electrical Resistance and Milk Progesterone," 1979, J. Dairy Sci., 62:64-68.

De Mol et al., "Application of Fuzzy Logic in Automated Cow Status Monitoring," 2001, J. Dairy Sci., 84:400-410.

O'Connor, "Heat Detection and Timing of Insemination for Cattle," 1993, Pennsylvania State University, Extension Circular 402.

Piccione et al., "Daily and Estrous Rhythmicity of Body Temperature in Domestic Cattle," 2003, BioMed Central, (8 pages).

Cooper-Prado et al., "Relationship of Ruminal Temperature with Parturition and Estrus of Beef Cows," 2011, J. Anim. Sci., 89:1020-1027.

http://ww.beaconhd.com.au/heatseeker.html, Beacon Heat Detectors, accessed on Feb. 27, 2014.

http://www.twilcanada.com/estrus-detector.php, Estrus Detector, accessed on Feb. 27, 2014.

http://www.cowchips.net/, How HeatWatch II Works, accessed on Feb. 27, 2014.

Bridges, et al., "Timed-Artificial Insemination in Beef Cows: What are the Options?," Purdue University Cooperative Extension Service, West Lafayette, IN (Rev Mar. 2008).

Fatakdawala, Hussain et al., "Hydrogen peroxide mediated transvaginal drug delivery," International Journal of Pharmaceutics 409 (2011) 121-127.

Hashimoto et al., "Oxidative stress induces gastric epithelial permeability through claudin-3." Biochemical and Biophysical Research Communications (2008), vol. 376, pp. 154-157.

Kadajji, et al., "Water Soluble Polymers for Pharmaceutical Applications." Polymers (2011), vol. 3, pp. 1972-2009.

SáFilho, O. G. et al., "Fixed-time artificial insemination with estradiol and progesterone for Bos indicus cows II: Strategies and factors affecting fertility," Science Direct, Theriogenology 72 (2009) 210-218.

Seth, et al., "Probiotics ameliorate the hydrogen peroxide-induced epithelial barrier disruption by a PKC-and MAP kinase-dependent mechanism," Am J Physiol Gastrointest Liver Physiol (2008), vol. 294, pp. G1060-G1069. Retrieved from http://www.ajpgi.org on Jul. 28, 2009.

* cited by examiner

IMPLANTABLE ESTRUS DETECTION DEVICES, SYSTEMS, AND METHODS

TECHNICAL FIELD

The present disclosure relates generally to implantable medical devices, and more particularly to devices, systems, and methods for detecting estrus.

BACKGROUND

In Vitro Fertilization (IVF) is a common procedure in animals and humans to increase the likelihood of pregnancy and/or to control certain aspects of a pregnancy. For example, in the case of animals such as cattle, IVF may be used to control the genetics of the offspring and thus the future makeup (e.g., gender ratio) of the herd. IVF may also be used to ensure that future offspring have the optimum characteristics for the production of either meat or milk. Thus, semen for use in IVF procedures may be selected based on desired offspring traits such as fast growth rate, high milk production, better overall health, and adaptations for the local climate.

In animals, the IVF process has to be performed by a skilled professional and is a time-consuming and intensive procedure for each animal. Accordingly, it would be beneficial to increase the success rate of these procedures, such that the valuable sperm and the time commitment from these professionals are most effectively used.

One of the factors influencing the success of any IVF procedure is the timing of insemination relative to the estrous cycle of the animal. Various biological changes take place within the animal that can influence the success of the IVF procedure. In order to ensure that these IVF procedures are carried out at a correct time, two main methods of estrous cycle monitoring/manipulation have emerged.

The first method aims to manipulate the natural estrous cycle of the animal such that the ideal insemination time can be predicted. A series of drugs are delivered to the animal(s) over the course of 10-14 days that force the reproductive cycle into a predictable pattern. This method allows the entire herd to be put onto the same cycle and therefore gives the ranch the ability to consolidate IVF procedures.

Another method involves attempting to monitor an animal's behavior and/or physiological symptoms in order to predict the cycle of an animal, such that insemination can be performed at an ideal time. For example, products are available that can be attached to an animal's back to detect "mounting events" (i.e., when cattle mount each other before becoming fully in heat), temperature, or activity. Vaginal tissue temperature or conductivity measurements may also be taken manually by ranch personnel.

These known products and procedures typically have a very high false positive rate. For example, temperature sensors are often triggered by changes in the environment, health, or activity of the animal, mounting detectors can be triggered by rubbing against trees and do not have very good resolution, and internal conductivity measurements have to be conducted manually and therefore can only be performed intermittently. While these products and procedures have shown some success in increasing pregnancy rates, data varies considerably depending on the way in which the product is implemented. Accordingly, there is a need for improved estrus sensing devices, methods, and systems that can be used to improve pregnancy rates in animals and groups of animals, such as cattle.

In humans, IVF is primarily used in cases where normal reproduction has not been successful. Human IVF procedures are extremely expensive and a failure can be emotionally devastating for those involved. While humans are more capable of measuring various biological factors (e.g., temperature) manually, it would also be desirable for women to have improved fertile window detection capabilities in order to increase the chance of pregnancy.

Accordingly, there is a need for improved estrus detection devices, systems, and methods that provide accurate estrous cycle monitoring and reduce the occurrence of false positives.

SUMMARY

In one aspect, methods of detecting an estrus condition of a subject are provided, including deploying in the subject an estrus detection device configured for intravaginal or intrauterine retention; sensing, via at least one sensor of the device, condition information of the subject; and determining an estrus condition of the subject using the condition information.

In another aspect, systems for detecting an estrus condition of a subject are provided, including at least one implantable estrus detection device configured for intravaginal or intrauterine deployment and retention in a subject. The device includes at least one sensor configured to detect condition information of a subject in whom or which it is implanted, and to determine an estrus condition of the subject using the condition information, wherein the at least one implantable estrus detection device is configured to communicate with a base station, other implanted estrus detection devices, or both, which are located within a reception radius thereof, regarding the determined estrus condition.

In yet another aspect, implantable estrus detection devices are provided, including a housing configured for intravaginal or intrauterine deployment and retention in a subject, and at least one sensor disposed in or on the housing, wherein the device is configured to use condition information sensed by the at least one sensor to determine an estrus condition of the subject.

DETAILED DESCRIPTION

The devices, systems, and methods described herein meet one or more of the above-stated needs by providing improved estrus detection for IVF procedures or insemination timing. In certain embodiments, internal implantable devices measure or sense certain condition information of the subject that may be used to determine as estrus condition of the subject. As used herein, the term "estrus condition"

refers to the phase of the estrous cycle when a female is physiologically sexually receptive. As used herein, the term "condition information" refers to any physiological or behavioral information relating to the subject, such as temperature, tissue conductivity, movement, activity, tissue color, pulse, and intravaginal pressure, among others, that may be used to determine whether the subject is experiencing estrus. That is, the implantable devices described herein use condition information from the subject (e.g., temperature, conductivity, movement, activity, color, pulse, pressure) to detect estrus of the subject in whom or which the device is implanted, so that insemination procedures may be performed at or near ideal conditions. In certain embodiments, the devices may be configured to receive biometric information about the subject in whom or which it is implanted, and/or to communicate with one another or with a base station, such that the estrus determination can be further tailored to the individual subject, environment, or herd behaviors.

In addition to detecting an estrus condition of the subject, the devices may also be capable of delivering a fluid, such as semen, drugs, and/or an egg, to the subject upon determination of the desired estrus condition. That is, the device may be designed to deliver semen to the subject upon detection of ideal estrus conditions, such that a subsequent and separate procedure is not necessary.

These devices advantageously are capable of collecting continuous, real time condition information without requiring multiple manual procedures to determine an estrus condition. Because the devices are implanted, and not externally affixed or attached to the subject, these devices are able to provide more accurate estrous cycle monitoring and reduce the occurrence of false positives.

Implantable estrus detection devices, and methods and systems for detecting estrus in subjects are described in more detail below.

Implantable Estrus Detection Devices

Figure 1A:
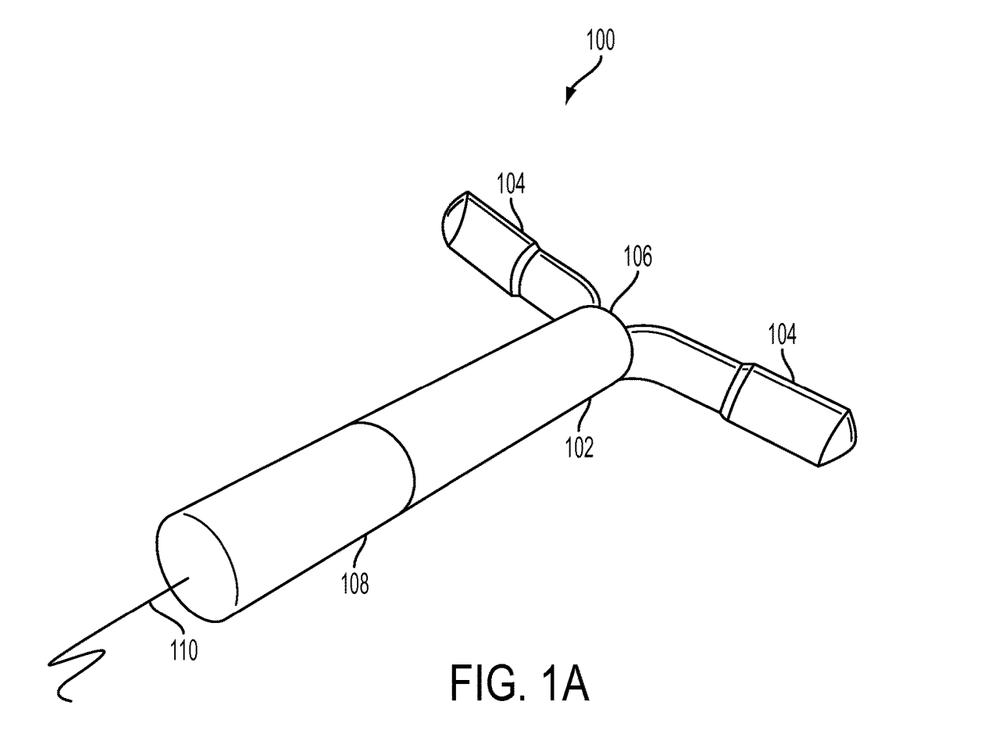
FIG. 1A is a perspective view of an implantable estrus detection device.
Figure 1B:
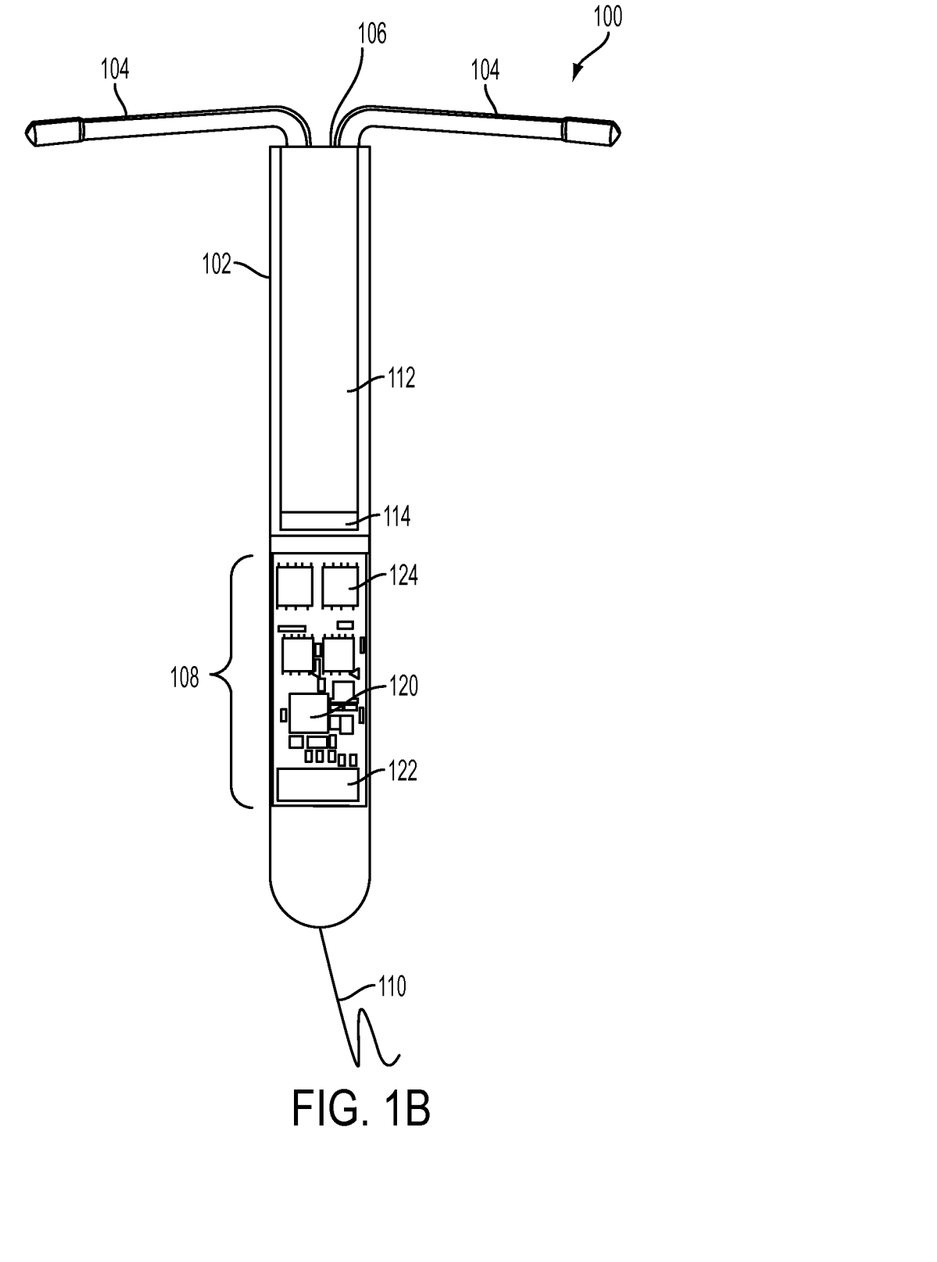
FIG. 1B is a cross-sectional view of the implantable estrus detection device of FIG. 1A.

In one aspect, implantable estrus detection devices are provided. In one embodiment, as shown in FIGS. 1A and 1B, a device 100 includes a housing 102 configured for intravaginal or intrauterine deployment and retention in a subject. For example, the housing may be sized and shaped for intravaginal or intrauterine deployment and retention in the subject. In one embodiment, the device 100 includes one or more retention features 104, for retaining the device upon deployment in a subject.

In certain embodiments, device 100 includes at least one sensor 120, 122, 124 disposed in or on the housing 102 and is configured to use condition information sensed by the at least one sensor 120, 122, 124 to determine an estrus condition of the subject. For example, the at least one sensor 120, 122, 124, may be provided at a sensor package 108 of the device opposite a fluid delivery mechanism 106. Alternatively, the at least one sensor may be located at any suitable device site that allows for collection of the condition information of interest.

In certain embodiments, the at least one sensor is selected from temperature sensors, conductivity sensors, color sensors, pulse sensors, activity sensors, mounting sensors, and pressure sensors. Other sensor types that may also provide condition information useful in the detection of an estrus condition are also envisioned. That is, a single device may include one, two, three, or more sensors configured to collect one or more types of condition information from the subject. In one embodiment, the device includes at least two sensors and is configured to use condition information sensed by the at least two sensors to determine an estrus condition of the subject, wherein the sensors are selected from the temperature sensors, conductivity sensors, color sensors, pulse sensors, activity sensors, mounting sensors, and pressure sensors.

Figure 2A:
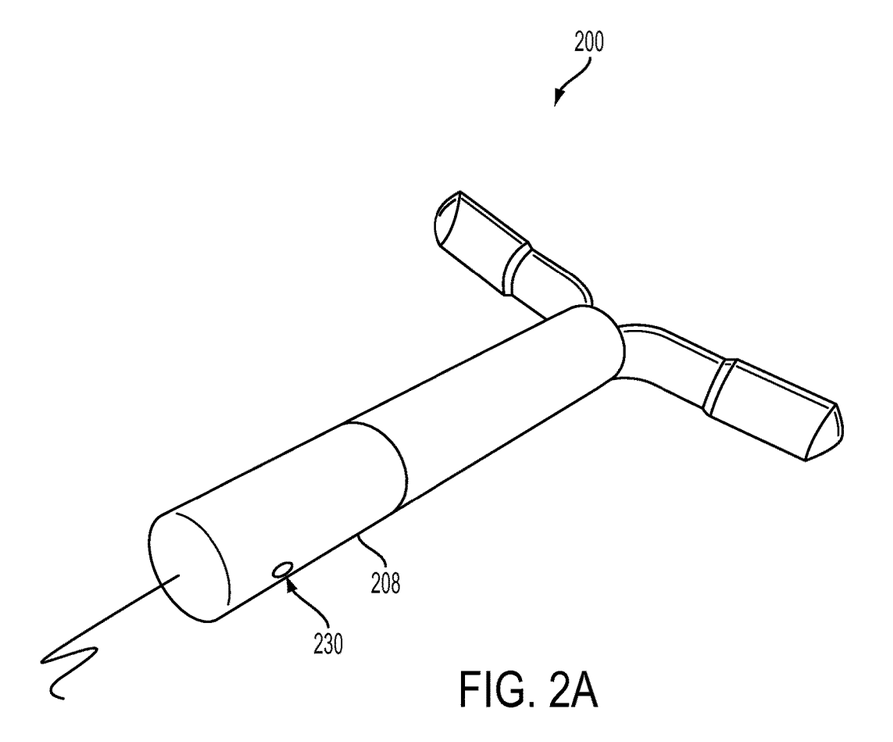
FIG. 2A perspective view of an implantable estrus detection device having a sensor port.
Figure 2B:
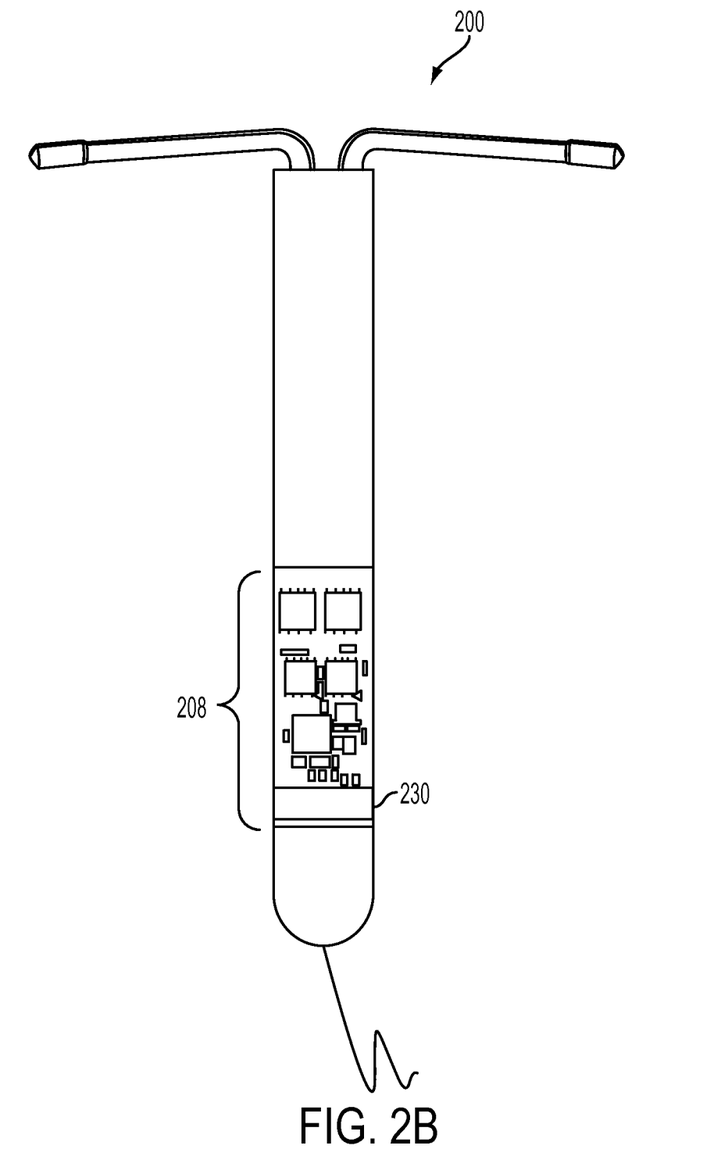
FIG. 2B is a cross-sectional view of the implantable estrus detection device of FIG. 2A.

In certain embodiments, as shown in FIGS. 2A and 2B, the device 200 also includes at least one port 230 in the housing via which at least one of the sensors or the sensor package 208 is in communication with surrounding vaginal or uterine tissue or fluid. For example, a temperature, conductivity, pressure, pulse, or color sensor may be provided such that at least a portion of the sensor is in communication with surrounding vaginal or uterine tissue or fluid.

Figure 3:
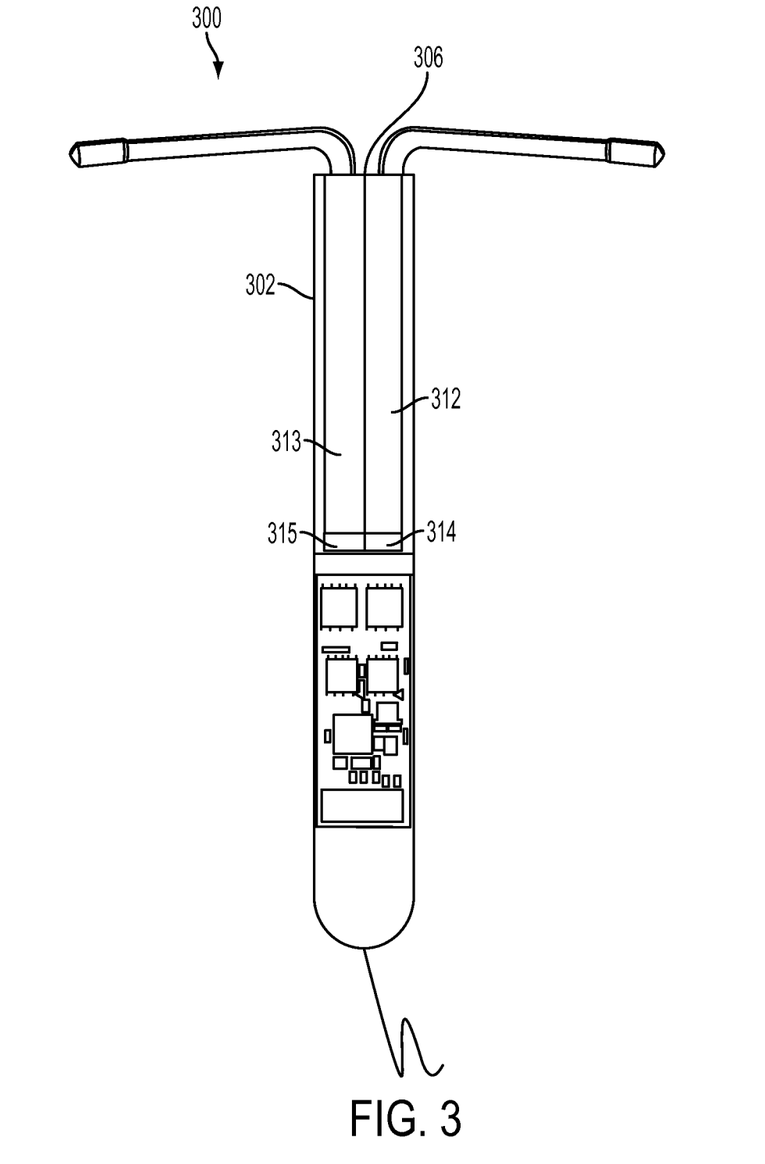
FIG. 3 is a cross-sectional view of an implantable estrus detection device having two fluid reservoirs.

In certain embodiments, as shown in FIGS. 1A and 1B, the device 100 includes a fluid delivery mechanism configured to dispense a fluid selected from drugs, semen, ova, and combinations thereof, when the estrus condition is determined to meet a predetermined threshold. For example, the fluid delivery mechanism may include a fluid reservoir 112 configured to house one or more fluids therein, as well as a fluid actuation mechanism 114, such as a piston or other mechanism to advance the fluid through the reservoir, and one or more outlets 106 via which the fluid(s) are delivered to the subject. In another embodiment, as shown in FIG. 3, the device 300 includes two fluid reservoirs 312, 314 and two respective fluid actuation mechanisms 314, 315, disposed within the housing 302, to dispense two fluids via outlet(s) 306. Fluid delivery mechanisms are described in more detail in co-pending application Ser. No. 14/448,087, filed on Jul. 31, 2014, entitled "Implantable Fluid Delivery Devices, Systems, and Methods," which is incorporated herein by reference in its entirety.

In certain embodiments, the device is configured to calculate the predetermined threshold based on information selected from biometric subject data, real time crowd data, historic data, modeling algorithms, and combinations thereof. For example, an implanted device may be configured to collect condition information on the subject, via the one or more sensors, and determine, based on biometric information about the subject, real time crowd and environment data, historic information, and modeling algorithms, among others, whether the subject is experiencing an estrus condition.

For example, the predetermined threshold of ideal estrus conditions for insemination may be determined using various existing estrous cycle models, such as those available in *Heat Detection and Timing of Insemination for Cattle*, Penn State College of Agricultural Sciences (1993). Such models may represent the various biological changes, such as in ovarian structures or hormone concentrations, that are associated with estrus, and provide guidance as to measurable physiological phenomenon that may be detected and equated with an estrus condition. For example, weightings of factors for individual animals, breeds, and/or herds can be recorded and customized. As part of the device setup, these factors and/or the predetermined threshold can be programmed directly into the device. Alternatively, the device can be configured to predict the predetermined threshold and thereby the date for estrus, based on more complex modeling, such as the modeling disclosed in Jun Ma, *A Method for Multiple Periodic Factor Prediction Problems Using Complex Fuzzy Sets*, IEEE Transactions on Fuzzy Systems, Vol. 20, No. 1, 32-45 (Feb 2012) and R. M. de Mol et al., *Applications of Fuzzy Logic in Automated Cow Status Monitoring*, J. Dairy Sci. 84:400-410 (2001).

Determination of the predetermined threshold may also include correlations or modeling from literature, depending on the sensor type to be used, as described below.

For example, temperature in cattle has been correlated to the estrous cycle; however, the vaginal temperature needs to be adjusted for variations in the overall body temperature of the animal and the environment. Literature models or correlations may be used to determine the predetermined threshold as it relates to temperature, including those disclosed in Brit H. Hoehmer, *Ruminal Temperature for Identification and Predication of Estrus in Beef Cows*, Master of Science Thesis, Oklahoma State University (July 2012), A. D. Fisher, et al. *Evaluation of a New Approach for the Estimation of the Time of the LH Surge in Dairy Cows Using Vaginal Temperature and Electrodeless Conductivity Measurements*, Theriogenology, Vol. 70, Issue 7, 1065-1074 (October 2008), Giuseppe Piccione, et al., *Daily and Estrous Rhythmicity of Body Temperature in Domestic Cattle*, BMC Physiology 3:7 (2003), and M. J. Cooper-Prado, *Relationship of Ruminal Temperature with Parturition and Estrus of Beef Cows*, J Anim. Sci., 89: 1020-1027 (2010). In determining an estrus condition, such temperature condition information may be adjusted for environmental temperature changes and/or for herd temperature changes. That is, data from the surrounding herd may be collected and a baseline normal mean temperature may be determined. For example, this can be done by the device itself as it gathers larger data sets or by a central computer, or base station, that will upload the data to the device. The predetermined threshold for each device therefore may be adjusted based on the environmental, herd data, modeling, and historic information, among others.

For example, intravaginal mucosal tissue conductivity has been correlated to the hormonal changes that indicate the onset of estrus. Electrical conductivity measurements may be taken on a variable frequency based on other factors. For example, since temperature may be a leading indicator given the steep curve of the electrical resistance measurement, the device may be configured to measure the electrical resistance only after some indication from other sensors indicate that estrus may be about to occur. For example, an electrical conductivity sensor may include two electrodes protruding from the device (e.g., via a port) that make contact with the mucosal tissue and pass a small voltage thereacross to measure conductivity. Literature models or correlations may be used to determine the predetermined threshold as it relates to temperature, including those disclosed in G. S. Heckman, et al., *Estrous Cycle Patterns in Cattle Monitored by Electrical Resistance and Milk Progesterone*, J. Dairy Sci., 62:64-68 (1979), and A. D. Fisher, et al. *Evaluation of a New Approach for the Estimation of the Time of the LH Surge in Dairy Cows Using Vaginal Temperature and Electrodeless Conductivity Measurements*, Theriogenology, Vol. 70, Issue 7, 1065-1074 (Oct 2008).

For example, activity and mounting events may be correlated with an estrus condition. Existing activity/mounting sensors are externally adhered and are highly susceptible to false positives, for example by cattle rubbing against a tree. Mounting events are expected to have a specific signature of movement. This is both an unusual position for an animal to be in and fairly high movement. When an event matches this signature, the mounting sensor may detect a mounting condition. For example, in the case of activity, it may be useful to adjust activity levels for the surrounding herd similar to the methods of adjusting temperature.

In the current devices, a three-axis accelerometer within the device may measure both activity and mounting events. For example, an ADXL345 (manufactured by Analog Devices, Norwood, Mass.) or KXTIA-1006 (manufactured by Kionix, Ithaca, N.Y.) accelerometer may be used. For example, the accelerometer may be set to record only data above a certain threshold, so that only significant events are recorded. For example, the accelerometer may be configured to sample and buffer acceleration data based on activity thresholds without microprocessor intervention, thus saving power overhead until motion thresholds have been detected. Such a configuration may advantageously allow the sensor to continuously monitor activity, yet keep the power levels and processing to a minimum, thereby extending the battery life of the device. For example, once the accelerometer detects motion, it can initiate the microprocessor to process the data, run the sensing algorithms, and then go back to an inactive status until needed again.

For example, intravaginal pressure may be correlated with estrus because as the animal reaches heat, the surrounding tissue swells and tightens. Though an exact value for expected pressures may not be known, the outside swelling of the vulva is noticeable, so the increase in pressure is expected to be fairly extreme (i.e., on the order of several psi), per Jane A. Parish, et al., *Estrus (Heat) Detection in Cattle*, Mississippi State University Extension Service (2010). For example, intravaginal pressure may be measured by a strain gauge applied to the inside of the device housing or to a more flexible membrane disposed on the housing. Alternatively, a balloon filled with air may also be disposed on the housing of the device, such that the air pressure may be recorded periodically.

For example, color or pulse may be correlated with estrus because swelling in the surrounding tissue occurs in which blood rushes the vagina and causes a change in chemical composition and color. For example, color or pulse may be detected using a low resolution camera and a small LED light. For example, an LED light in the proximity of the tissue may be activated and the color of the light reflected may be recorded by the camera. Changes in color may then be used to infer the heart rate of the animal or the oxygen content of the blood through colorimetric data.

A single device may have one or more sensors disposed in or on the housing, to collect one or more types of condition information about the subject. Depending on the condition information collected, the device, or an external computer system or base station, may determine whether an estrus condition is present in the subject, based on any combination of individual, herd, environment, modeling, historic, or other factors. For example, a predetermined threshold may be calculated based on the real time crowd data, wherein calculating the predetermined threshold based on the real time crowd data comprises adjusting an expected threshold for an estrus condition based on the real time crowd data for that estrus condition to determine the predetermined threshold for an estrus condition.

In certain embodiments, as shown in FIGS. 1A and 1B, the device 100 includes an antenna 110 configured to transmit information to and/or receive information from other implantable estrus detection devices, a base station, or both. For example, the antenna may be internal or external to the device housing. In certain embodiments, the antenna 110 includes, or is formed as, an external device retrieval member. Alternatively, a retrieval member that is not an antenna may be provided. That is, the retrieval member may allow a professional to remove the device from the implantation site in the subject. For example, the retrieval member may include a loop or other retrieval feature.

Suitable device features, including housing designs, retention features, antennae, retrieval members, and fluid dispensing mechanisms, are disclosed in U.S. application Ser. No. 13/629,124, filed on Sep. 27, 2012, entitled "Single Channel, Multiple Drug Delivery Device and Methods", application Ser. No. 13/629,159, filed on Sep. 27, 2012, entitled "Multiple Reservoir Drug Delivery Device and Methods", U.S. application Ser. No. 13/629,184, filed on Sep. 27, 2012, entitled "Drug Reconstitution and Delivery Device and Methods", U.S. application Ser. No. 13/742,203, filed on Jan. 15, 2013, entitled "Devices and Methods for Intraluminal Retention and Drug Delivery" (29833-0033), U.S. application Ser. No. 14/071,929, filed on Nov. 5, 2013, entitled "Fluid Delivery Devices and Methods", and U.S. application Ser. No. 14/107,367, filed on Dec. 16, 2013, entitled "Electrolytic Gas Generating Devices, Actuators, and Methods", each of which is incorporated herein by reference in its entirety.

Methods of Detecting Estrus

In another aspect, methods of detecting an estrus condition of a subject are provided. In one embodiment, a method includes deploying in the subject an estrus detection device configured for intravaginal or intrauterine retention, sensing, via at least one sensor of the device, condition information of the subject, and determining an estrus condition of the subject using the condition information. The device may include any combination of device features discussed above.

In one embodiment, the method also includes programming the device with biometric information, identification information, or both, about the subject. For example, in the case of livestock, the subject's age, weight, or other relevant biometric information may be programmed into the device. For example, the device may be programmed with identification information to allow for the collection of individualized data and/or for tracking purposes.

In certain embodiments, the sensing includes sensing, via at least two sensors, condition information of the subject, and the at least two sensors are selected from temperature sensors, conductivity sensors, color sensors, pulse sensors, activity sensors, mounting sensors, and pressure sensors.

In certain embodiments, the method also includes dispensing a fluid when the estrus condition of the subject meets a predetermined threshold. For example, the fluid may be selected from drugs, semen, ova, and combinations thereof In certain embodiments, the method also includes calculating the predetermined threshold based on information selected from biometric subject data, real time crowd data, historic data, modeling algorithms, and combinations thereof In one embodiment, the method includes receiving real time crowd data from one or more other implanted estrus detection devices, a base station, or both, which is located within a reception radius of the device, and calculating the predetermined threshold based on the real time crowd data, wherein calculating the predetermined threshold based on the real time crowd data comprises adjusting an expected threshold for an estrus condition based on the real time crowd data for that estrus condition to determine the predetermined threshold for an estrus condition.

In one embodiment, the method includes receiving the predetermined threshold from a base station, which is located within a reception radius of the device, wherein the predetermined threshold has been calculated based on real time crowd data received by the base station from one or more implanted estrus detection devices.

In one embodiment, the method includes transmitting the determined estrus condition of the subject to another implanted estrus detection device, a base station, or both.

Systems for Detecting Estrus

Figure 4:
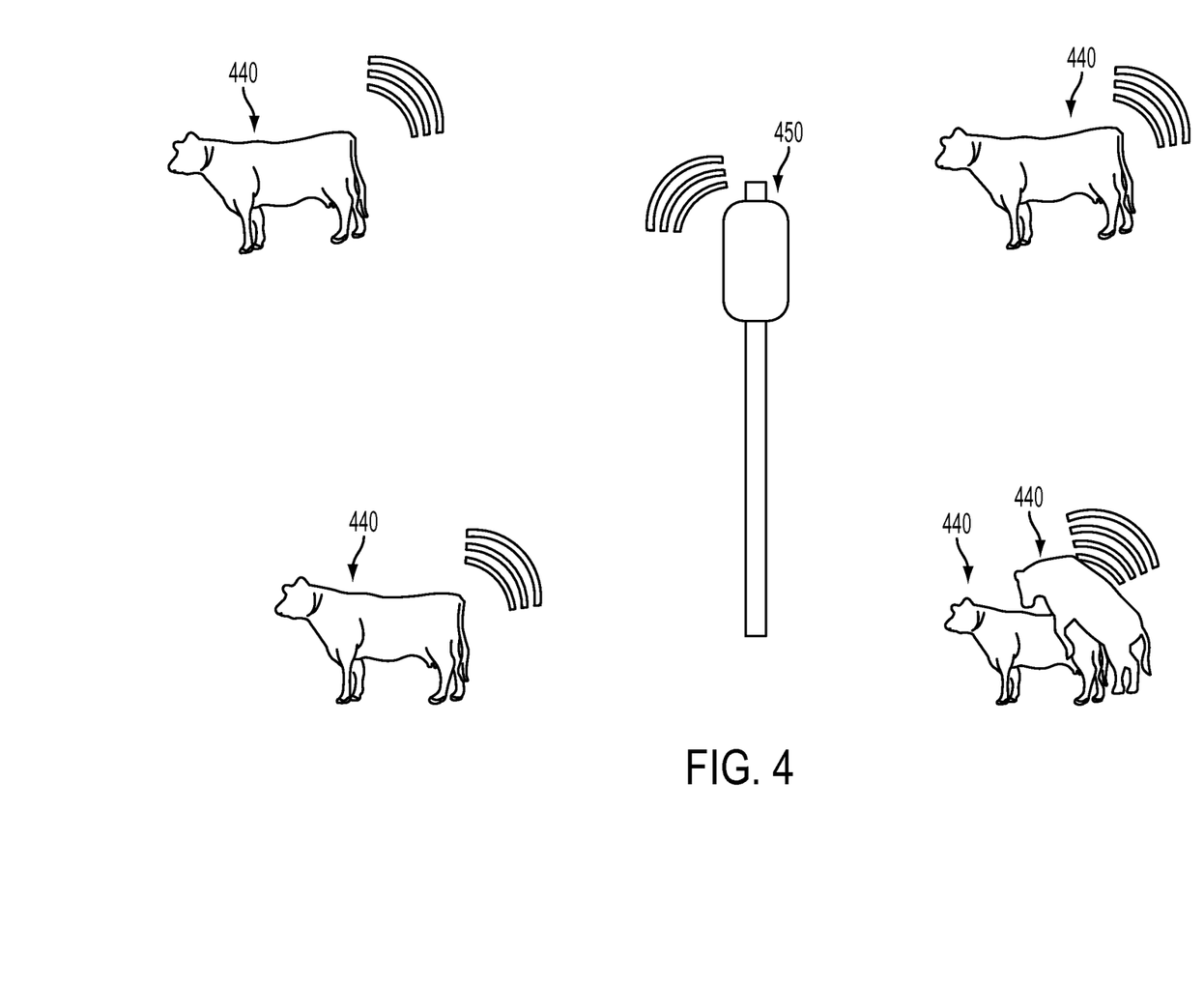
FIG. 4 is an illustration of a system for detecting estrus in a subject.

In another aspect, a system for detecting an estrus condition of a subject is provided. In certain embodiments, as shown in FIG. 4, the system includes at least one implantable estrus detection device 440 (shown implanted in subjects) configured for intravaginal or intrauterine deployment and retention in a subject, the device comprising at least one sensor configured to detect condition information of a subject in whom or which it is implanted, and determine an estrus condition of the subject using the condition information, wherein the at least one implantable estrus detection device 440 is configured to communicate with a base station 450, other implanted estrus detection devices 440, or both, which are located within a reception radius thereof, regarding the determined estrus condition.

In one embodiment, the system includes at least two of the implantable estrus detection devices, and the base station, the implantable estrus detection devices, or both, are configured to calculate an expected estrus condition threshold value based on condition information from the implantable estrus detection devices. That is, the system may use the real time information collected to calculate or adjust a baseline estrus condition threshold, against which the condition information about an individual subject may be compared, to determine whether the subject is in estrus.

In one embodiment, each implantable estrus detection device is configured to collect condition information from the implantable estrus detection devices within a reception radius thereof, and to transmit the collected condition information to the base station when it comes within a reception radius thereof.

In one embodiment, before being inserted, the device may communicate wirelessly with a base station and may be programmed with some basic information about the animal (e.g., weight, breed, herd/pen, serial number). This information may be useful in matching the individual's condition information to expected values or communicating amongst other animals that might be undergoing the same conditions. In certain embodiments, devices are implanted in animals at various phases in the estrous cycle, including animals that are not currently in estrus. The "off cycle" animals may be used as a control to calibrate activity and temperature readings.

In one embodiment, each device communicates with a central antenna, or base station, located near the animals or near a central location. A central sever may analyze condition information from all the animals and compute adjustments that might be needed for various sensors. The central server may also keep track of any systematic adjustments that might be needed for a specific animal, breed, or herd for future work. This communication need not be continual. For example, the check-in frequency of the devices may be balanced with battery life to ensure that the devices can survive. For example, the device may record events every 15 seconds and have a lifetime of 29 days.

In one embodiment, since animals may be out to pasture and not within communication range of a central server or base station, the animals with the implanted devices could also form an ad-hoc network with any surrounding animals. Though the smaller network may not be as accurate, a small population of animals will allow for some adjustment of temperature readings and other data. For example, protocols such as ZIGBEE may support this type of networking.

In another embodiment, the ad-hoc network allows animals within close proximity of each other to communicate and share all their information with each other. When one of the animals wanders within the range of a master antenna, or base station, it will upload this data and the master network can also download additional matching data to the animal. The animal can then communicate this additional data to other animals it might come into contact with.

In certain embodiments, the implantable devices can also communicate with larger devices strapped to the animal's neck. Because of the increased size of the external device, these external devices can carry larger batteries and have significantly larger range of communication. For example, for free range cattle, the animals could be up to a mile from the base station, but occasionally send data collected to the base station.

The disclosed devices, methods, and systems advantageously provide improved estrus detection in subjects. Using internal, implantable devices having at least one, and in certain cases many, sensors, the occurrence of false positive can be reduced and the ideal insemination timing can be predicted. Moreover, the devices may have the ability to dispense a fluid, such as semen, to a subject upon determining of estrus. The ability of the devices to communicate with one another, or with a base station that is communicating with other devices, improves the accuracy of the estrus detection by allowing for adjustment of the predetermined condition threshold for particular condition information, based on environmental or herd factors, among others. Accordingly, the success rate of IVF procedures may be improved and the amount of semen and the time required of professionals may be reduced.

It will be appreciated that variants of the above-disclosed and other features and functions, or alternatives thereof, may be combined into many other different devices, systems, methods, or applications. Various presently unforeseen or unanticipated alternatives, modifications, variations, or improvements therein may be subsequently made by those skilled in the art which are also intended to be encompassed by the following claims.

We claim:

1. A method of detecting an estrus condition of a subject, comprising:
   programming an estrus detection device configured for intravaginal or intrauterine retention with biometric information about the subject;
   deploying the device in the subject;
   calculating a predetermined threshold of estrus conditions for insemination by the device using the biometric information;
   sensing, via at least one sensor of the device, condition information of the subject; and
   determining an estrus condition of the subject using the condition information.

2. The method of claim 1, further comprising:
   programming the device with identification information about the subject.

3. The method of claim 1, wherein the at least one sensor is selected from temperature sensors, conductivity sensors, color sensors, pulse sensors, activity sensors, mounting sensors, and pressure sensors.

4. The method of claim 1, wherein:
   the sensing comprises sensing, via at least two sensors, condition information of the subject, and
   the at least two sensors are selected from temperature sensors, conductivity sensors, color sensors, pulse sensors, activity sensors, mounting sensors, and pressure sensors.

5. The method of claim 1, further comprising:
   dispensing a fluid when the estrus condition of the subject meets the predetermined threshold,
   wherein the fluid is selected from drugs, semen, ova, and combinations thereof.

6. The method of claim 5, further comprising:
   calculating the predetermined threshold based on at least one of real time crowd data, historic data, and modeling algorithms.

7. The method of claim 5, further comprising:
   receiving real time crowd data from one or more other implanted estrus detection devices, a base station, or both, which is located within a reception radius of the device; and
   wherein calculating the predetermined threshold includes calculating the predetermined threshold based on the real time crowd data and comprises adjusting an expected threshold for an estrus condition based on the real time crowd data for that estrus condition to determine the predetermined threshold for an estrus condition.

8. The method of claim 1, further comprising transmitting the determined estrus condition of the subject to another implanted estrus detection device, a base station, or both.

9. A system for detecting an estrus condition of a subject, comprising:
   at least one implantable estrus detection device programmed with biometric information about the subject and configured for intravaginal or intrauterine deployment and retention in a subject and configured to calculate an expected estrus condition threshold value, the device comprising at least one sensor configured to detect condition information of the subject, and determine an estrus condition of the subject using the condition information of the subject,
   wherein the at least one implantable estrus detection device is configured to communicate with a base station, other implanted estrus detection devices, or both, which are located within a reception radius thereof, regarding the determined estrus condition, and
   wherein the at least one implantable estrus detection device is configured to collect condition information from other implantable estrus detection devices within a reception radius thereof, and to transmit the collected condition information to the base station when it comes within a reception radius thereof.

10. The system of claim 9, wherein:
    the system comprises at least two of the implantable estrus detection devices.

11. An implantable estrus detection device, comprising:
    a housing configured for intravaginal or intrauterine deployment and retention in a subject;
    at least one sensor disposed in or on the housing; and
    a fluid delivery mechanism configured to dispense a fluid when an estrus condition is detected in the subject and determined to meet a predetermined threshold,
    wherein the device is configured to use condition information sensed by the at least one sensor to determine an estrus condition of the subject, and
    wherein the device is configured to calculate the predetermined threshold based, at least in part, on biometric subject data.

12. The device of claim 11, wherein the at least one sensor is selected from temperature sensors, conductivity sensors, color sensors, pulse sensors, activity sensors, mounting sensors, and pressure sensors.

13. The device of claim 11, wherein the device comprises at least two sensors and is configured to use condition information sensed by the at least two sensors to determine an estrus condition of the subject, the sensors being selected from temperature sensors, conductivity sensors, color sensors, pulse sensors, activity sensors, mounting sensors, and pressure sensors.

14. The device of claim 11, further comprising at least one port via which the at least one sensor is in communication with surrounding vaginal or uterine tissue or fluid.

15. The device of claim 11, wherein the fluid is selected from drugs, semen, ova, and combinations thereof.

16. The device of claim 15, wherein the device is configured to calculate the predetermined threshold based on at least one of real time crowd data, historic data, and modeling algorithms.

17. The device of claim 11, further comprising an antenna configured to transmit information to and/or receive information from other implantable estrus detection devices, a base station, or both.

18. The device of claim 17, wherein the antenna comprises an external device retrieval member.

* * * * *